United States Patent
Udayakumar et al.

(10) Patent No.: US 9,259,512 B2
(45) Date of Patent: Feb. 16, 2016

(54) LUBRICATING DEODORANT FOR OSTOMY POUCHES

(75) Inventors: Bettakeri Subraya Udayakumar, Darien, IL (US); Margo Elaine Love, Uni, UT (US)

(73) Assignee: Hollister Incorporated, Libertyville, IL (US)

( * ) Notice: Subject to any disclaimer, the term of this patent is extended or adjusted under 35 U.S.C. 154(b) by 1374 days.

(21) Appl. No.: 12/038,623

(22) Filed: Feb. 27, 2008

(65) Prior Publication Data

US 2008/0161764 A1 Jul. 3, 2008

Related U.S. Application Data

(63) Continuation of application No. 10/608,706, filed on Jun. 27, 2003, now Pat. No. 7,422,577.

(51) Int. Cl.
*A61F 5/441* (2006.01)
*A61L 28/00* (2006.01)

(52) U.S. Cl.
CPC ............ *A61L 28/0034* (2013.01); *A61F 5/441* (2013.01)

(58) Field of Classification Search
CPC . A61F 5/44; A61F 5/4401; A61F 2005/4402; A61F 5/4404; A61F 5/4405; A61F 5/4407; A61F 5/4408; A61F 5/441; A61F 2005/4415; A61F 5/442; A61F 5/445; A61F 2005/4455; A61F 5/448; A61F 2005/4483; A61F 2005/4486; A61F 5/449; A61F 2005/4495; A61F 5/451; A61L 28/0061; A61L 28/0069; A61L 28/0007; A61L 28/0019; A61L 28/003; A61L 28/0034; A61L 28/0038

See application file for complete search history.

(56) References Cited

U.S. PATENT DOCUMENTS

| 4,851,214 | A | * | 7/1989 | Walters et al. ................ 424/65 |
| 4,906,462 | A | | 3/1990 | Miki et al. |
| 5,582,820 | A | | 12/1996 | Yamamoto et al. |
| 6,129,716 | A | | 10/2000 | Steer |
| 6,200,939 | B1 | * | 3/2001 | Maurer .......................... 510/161 |
| 6,344,218 | B1 | * | 2/2002 | Dodd et al. .................... 424/605 |
| 6,852,100 | B1 | * | 2/2005 | Gent et al. ..................... 604/333 |
| 2002/0176879 | A1 | | 11/2002 | Dodd et al. |
| 2003/0049290 | A1 | * | 3/2003 | Jha et al. ....................... 424/401 |
| 2004/0062681 | A1 | | 4/2004 | Winston |

FOREIGN PATENT DOCUMENTS

| EP | 0 790 047 A1 | 8/1997 |
| EP | 0 850 613 A1 | 7/1998 |
| EP | 1 013 249 A1 | 6/2000 |
| EP | 1088560 A1 | 4/2001 |
| EP | 1 101 462 A1 | 5/2001 |
| GB | 1032037 | 6/1966 |
| JP | 9-202721 A | 8/1997 |
| WO | WO 01/60373 A1 | 8/2001 |
| WO | WO 03/020231 A2 | 3/2003 |

OTHER PUBLICATIONS

Polyethylene glycol, Sigma Aldrich, 2014.*
Search Report from PCT/US2004/015687, mailed Oct. 27, 2004 (5 pages).
Written Opinion from PCT/US2004/015687, mailed Oct. 27, 2004 (6 pages).
Material Safety Data Sheet, "O.A.D.®", Coloplast Corp., Marietta, Georgia, May 8, 2002.
English-language translation of Office Action for corresponding Japanese Application No. 2002-573050, dated Sep. 16, 2009.
Office Action for corresponding Australian Application No. 2004255536, dated May 27, 2009.

* cited by examiner

*Primary Examiner* — Susan Tran
*Assistant Examiner* — William Craigo
(74) *Attorney, Agent, or Firm* — Levenfeld Pearlstein, LLC

(57) ABSTRACT

A lubricating deodorant for ostomy pouches in the form of an aqueous solution which contains both a water-soluble lubricating agent and a compatible water-soluble complexing agent capable of complexing with and neutralizing the odor-causing molecules of fecal matter. Other surfactants, preservatives, humectants and pH-adjusting agents may also be included. The method of using such a lubricating deodorant solution is also disclosed.

3 Claims, No Drawings

LUBRICATING DEODORANT FOR OSTOMY POUCHES

REFERENCE TO RELATED APPLICATIONS

This is a Continuation of U.S. patent application Ser. No. 10/608,706, filed Jun. 27, 2003.

BACKGROUND AND SUMMARY

Deodorizing compositions for use in ostomy pouches are known in the art as disclosed, for example, in U.S. Pat. No. 6,129,716 (Steer) and U.S. Pat. No. 6,200,939 (Maurer). They are especially beneficial when used with drainable pouches designed to be periodically emptied and cleaned for reuse. Such procedures subject ostomates and/or caregivers to malodors from the pouches' contents as fecal materials become exposed to air. The malodor problems which the deodorizing agents are intended to reduce are only exacerbated by the tendencies of fecal matter to stick or cling to the inner surfaces of ostomy pouches, thereby prolonging exposure to such malodors during emptying and cleaning procedure.

Apart from such odor problems, users have also encountered difficulties when opposite inside surfaces of pouches stick or block together and thereby obstruct the entry and downward movement of fecal matter discharged into the pouches. Also, feces sometimes cling to opposing pouch surfaces, resulting in a "pancaking" action that impedes downward travel of fecal material. It has long been known that users, in their efforts to reduce such blocking and sticking problems, have sometimes resorted to coating interior pouch surfaces, or at least surfaces opposite from the stoma openings, with anti-sticking agents such as those commonly found in the home. For example, it is recognized that a material widely marketed under the trademark "Pam" has been sprayed by users into ostomy pouches through the stoma-receiving openings thereof before such pouches are adhered to the skin. One disadvantage is that such oily anti-sticking agents are also capable of traveling to the heat seals at the edges of the pouches and become absorbed by the polymeric materials from which such pouches are formed, thereby weakening the heat seals and increasing the risk of possible rupture of the pouches in use.

Other approaches had been proposed for reducing the coefficient of surface friction and possible adhesion between the walls of ostomy pouches. Reference may be had to published International application WO 03/026540 (Andersen et al.) where a hydrophilic coating is adhesively applied to one or more interior surface portions at the time of pouch manufacture. One disadvantage is that such a hydrophilic coating requires substantial moisture to become hydrated and lubricious, so the beneficial effects may not be realized unless the waste material discharged into a pouch is sufficiently liquid to activate the hydrophilic coating material.

Other patents and published applications disclosing or suggesting various approaches for reducing frictional resistance to movement of waste material in ostomy pouches are U.S. Pat. Nos. 5,348,546, 4,518,388, 5,001,009, and European Patents 0 991 701, and 0 272 816. While these references in one way or another address the issue of sticking, none is concerned with a material or procedure in which odor neutralizing also occurs simultaneously, or in which an aqueous composition has components that coact with each other to achieve and enhance both results.

A main aspect of this invention is to provide an ostomy pouch lubricating deodorant that takes the form of an aqueous solution of a water-soluble lubricating agent and a water-soluble complexing agent capable of complexing with and neutralizing the odor-causing molecules of fecal matter. Such a liquid lubricating deodorant is placed into a pouch, ordinarily a drainable pouch, by the user. If the ostomy appliance is a one-piece appliance (where the pouch is permanently connected to an adhesive faceplate), then the user of a fresh pouch may introduce the recommended amount of liquid lubricating deodorant into the pouch through its stoma-receiving opening prior to adhering the pouch to the skin. When the pouch thereafter needs draining and cleaning, a process that results in a loss of at least some of the liquid deodorizing/lubricating agent, the desired amount of such agent may be replenished by introducing it through the pouch's drainage opening. If the appliance is a two-piece appliance (where the pouch is detachable from the faceplate), the deodorizing lubricant may be introduced into the pouch either through the pouch's stoma-receiving opening or through its drainage opening if there is one.

In a particularly effective embodiment of the invention, the water-soluble complexing agent that acts to neutralize the odor-causing molecules of fecal matter is also a surfactant and, as a surfactant, coacts with the water-soluble lubricating agent to enhance the lubricating effectiveness of the latter. In addition, the liquid lubricating and deodorizing solution may contain other surfactants, humectants, hydrating agents, preservatives, and pH-adjusters or buffers.

Other features, advantages and objects of the invention will become apparent from the following description.

DETAILED DESCRIPTION OF PREFERRED EMBODIMENTS

The odor-neutralizing lubricant of this invention essentially comprises an aqueous solution of a lubricating agent and a complexing agent capable of neutralizing the odor-causing molecules or fecal matter. In addition, the solution includes one or more surfactants and, ideally, the complexing agent also has surfactant capabilities for enhancing both the lubricating and deodorizing functions of the liquid composition.

The lubricating agent may take the form of an aqueous solution of any of a number of cellulosic material such as hydroxyethylcellulose (e.g., "Natrosol 250" from Hercules Incorporated, Wilmington, Del.), hydroxypropylmethylcellulose ("Methocel K15M Premium" from Dow Chemical), or hydroxypropylcellulose. Aqueous solutions of other hydrophilic polymers such as polyethylene oxide ("Polyox WSR 1105" from Union Carbide) may also be used. Effective results may also be obtained with aqueous solutions of polymeric ethers, polyvinyl, alcohol, polyvinylpyrrolidone, hydrophilic colloids and their derivatives, synthetic polymers, polyols and carbomers, and their combinations.

Such lubricating agents are sometimes regarded as thickeners or viscosity-boosting agents; however, they also have the characteristic of becoming slippery or lubricious when hydrated sufficiently to form viscous solutions. The extent of dilution, and hence the particular viscosity achieved, is not considered critical as long as the lubricating agent remains a flowable liquid that is capable of wetting and, to a greater or lesser extent, clinging to the inner wall surfaces of an ostomy pouch. The polymeric film materials from which such walls are formed are well known and may vary considerably but, in general, such films may be multilayer or mono-layer and are liquid and gas (especially odor) impermeable.

The odor neutralizer in preferred embodiments of this invention should take the form of a water-soluble complexing agent capable of complexing with and neutralizing the odor-causing molecules of fecal matter thereby reducing their concentration in the vapor phase. In performing that function, the complexing agent reacts directly with the odor-causing molecules, in contrast to serving merely as a perfume or odor-masking agent. Particularly effective neutralizers are found to be materials such as n-ethyl-n-soya-morpholinium ethosulfate, copper citrate, and vegetable protein extracts, but other ionic and nonionic compounds and protein derivatives and extracts and their combinations may be used. Where the odor neutralizer functions as a surfactant, it also serves to enhance the lubricating effectiveness of the lubricating agent as well as its own effectiveness as an odor neutralizer. Especially effective in this regard is n-ethyl-n-soya-morpholinium ethosulfate which functions as a cationic surfactant and is available under the trademark "Forestall" (Uniqema, New Castle, Del.).

It has also been found that the surfactant or wetting properties are enhanced if a plurality of surfactants are provided in contrast to using only a higher concentration of a single surfactant. Such surfactants may be anionic, cationic, nonionic or amphoteric, or a combination thereof. Examples include, but are not limited to, octoxynol-9, poloxamer 188, sorbitan monolaurate, and alkyl dimethylamine oxide.

Other ingredients include preservatives which prevent microbial growth and add shelf life, for example, methylparaben, ethylparaben, propylparaben, butylparaben, isobutylparaben, phenoxyethanol or a blend of two or more of such preservatives. One such blend found to be suitable is sold under the trademark "Phenonip" by Clariant Corporation, Charlotte, N.C. Any of a variety of other well-known preservatives may also be used. Further, it is desirable to include propylene glycol not only for its solvent hydrating effect but also as a preservative; however, other agents having similar properties may be used, such as glycerine or butylene glycol.

The pH of the aqueous mixture should be neutral, or approximately neutral, so, depending on the particular ingredients selected, pH adjusters and buffers may be added as needed, all as well known in the art.

The lubricating deodorant of this invention may be conveniently supplied to users in a bottle or tube, preferably in a plastic squeeze bottle with a dispensing closure for ease of application. Alternatively, the lubricating deodorant may be packaged in unit-of-use packets for the benefit of ostomates at work or traveling who might find such packets less cumbersome to carry and use than squeeze bottles. The ostomate or caregiver is instructed to introduce a small amount of the viscous liquid, preferably about 5 ml (1 tsp) and more generally an amount within the range of about 3 to 10 ml, into an ostomy pouch either through the stoma opening of the pouch, before it is adhesively attached to the skin, or through the drainage opening of the pouch after it has been so attached to the skin. Of course, if the pouch is a closed or non-drainable pouch, then the only available procedure is the first of these. The drain opening (if there is one) is then closed and the user rubs or squeezes the walls of the pouch to coat its inside surfaces with the liquid lubricating deodorant. Later, when emptying of a drainable pouch is required, the drainage neck of the pouch is unrolled or unclamped and the contents of the pouch are discharged into a toilet, the lubricating deodorant allowing such action to occur by gravity with little or no squeezing action by the fingers against the outside wall surfaces of the pouch being necessary for discharging the pouch's contents. Thereafter, an additional amount of lubricating deodorant is introduced into the pouch through its discharge opening to replenish the amount lost during the emptying and cleaning steps.

In general, a lubricating deodorant embodying this invention should contain a weight percentage of cellulosic or other water-soluble lubricating agent in the weight percentage range of approximately 0.1 to 5.0 percent and a complexing and odor-neutralizing agent within the range of about 0.2 to 7 percent. One or more additional surfactants may be and preferably are included, having a combined weight of up to about 15 percent, preferably about 0.1 to 10 percent. A humectant-solvent such propylene glycol may be present in the approximate range of 0.5 to 20 percent, and a preservative may account for about 0.03 to 1.0 percent by weight. Purified water is a major component in terms of weight, amounting to about 58 to 98 percent of the solution's total weight.

The following examples further illustrate important features of this invention:

EXAMPLE 1

One hundred grams (100 g) of a liquid lubricating deodorant for ostomy pouches embodying the invention may be prepared using the following ingredients:

| Ingredient | Percent W/W |
|---|---|
| Purified Water | 75.00 |
| Hydroxyethylcellulose [Natrosol 250 HHX] | 0.70 |
| Propylene Glycol | 3.00 |
| Poloxamer 188 NF [Pluronic F-68] | 2.00 |
| Octoxynol-9 [Triton X-100] | 0.30 |
| n-ethyl-n-soya-morpholinium ethosulfate [Forestall] | 1.50 |
| Phenonip | 0.30 |
| 0.5 N sodium hydroxide solution to bring product pH to 7.00 ± 0.25 range | 0.2747 |
| Purified Water (QS. to 100 g batch wt.) | 16.9253 |
| TOTAL | 100 |

In a 250 ml beaker quipped with mechanical stirrer is placed 75 g of purified water. With stirring, is then added 0.70 g hydroxylethylcellulose. The ingredients are mixed for 15 minutes and the solution is warmed to 40° C. Heating is discontinued and 1.5 g of propylene glycol is added and mixed for 60 minutes. While mixing, 1.5 g of Forestall, 1.5 g of propylene glycol, 2.0 g of poloxamer 188 NF, and 0.3 g of Phenonip are added. The pH of the aqueous liquid is then adjusted to 7.00 (plus or minus 0.25) and purified water is added to produce a 100 g batch weight. Mixing is continued for an additional 30 minutes before packaging the product in 8 oz. bottles.

EXAMPLE 2

Another example of lubricating deodorant solution embodying the invention may be prepared with the following ingredients:

| Ingredient | Percent W/W |
|---|---|
| Purified Water | 75.00 |
| Hydroxypropymethylcellulose [Methocel K15M Premium] | 1.20 |
| Propylene Glycol | 3.00 |
| Octoxynol-9 [Triton X-100] | 0.30 |
| n-ethyl-n-soya-morpholinium ethosulfate [Forestall] | 1.50 |
| Phenonip | 0.30 |
| 0.5 N sodium hydroxide | 0.34 |
| Purified Water (QS. to 100 g batch wt.) | QS to 100 g |
| TOTAL | 100 |

The procedure for preparing this solution is essentially the same as set forth in Example 1 except that hydroxypropylmethylcellulose is substituted for hydroxyethylcellulose as the lubricating agent.

EXAMPLE 3

A further example of a lubricating deodorant embodying the invention, this one using vegetable protein extract as the odor neutralizer, may be prepared as set forth in Example 1 with the following ingredients:

| Ingredient | Percent W/W |
|---|---|
| Purified Water | 75.00 |
| Hydroxyethylcellulose [Natrosol 250 HHX] | 0.70 |
| Propylene Glycol | 3.00 |
| Poloxamer 188 NF | 2.00 |
| Octoxynol-9 | 0.30 |
| Phenonip | 0.30 |
| Vegetable Protein Extract C 1575 [Carrubba] | 5.00 |
| Sodium Citrate | 0.24 |
| Purified Water | QS. to 100 g |
| TOTAL | 100 |

EXAMPLE 4

The effectiveness of the lubricating deodorant prepared in accordance with Example 1 has been tested by using globs or lumps of refried beans paste to simulate feces and comparing the drop time and drain time of such paste in drainable ostomy pouches with and without added lubricating deodorant (LD) of this invention. The tests were conducted with three drainable ostomy pouches (Hollister pouch 3669) with pouch 1 being dry (i.e., no lubricating deodorant added) and pouches 2 and 3 respectively receiving 5.102 g and 5.452 g of lubricating deodorant.

In conducting the test, the pouches were hung by clamps on a horizontal rod. Measured amounts of lubricating deodorant were then squeezed into each of the pouches 2 and 3 through their bottom openings. Thereafter, the bottom drain openings of the pouches were closed using pouch clamps. The pouches were then rubbed gently by hand to spread the lubricating deodorant throughout the interiors of the pouches.

Beans paste (Vegetarian Refried Beans, Jewel brand) was then loaded into a modified syringe. (The modification consisted of cutting a 25 cc disposable syringe transversely near its needle end so that the opening at the end of the barrel was of the same diameter as the interior of the barrel.) The beans paste was manually loaded into the syringe from its front end using a spatula. The amount of beans paste loaded into the syringe was recorded and the paste was then discharged into the interior of each pouch through its faceplate opening. Timing was commenced at the moment the paste was discharged in a pouch and was discontinued when the paste stopped moving inside that pouch. After three successive loads of paste into each pouch, with drop time being measured for each load, the drain time was determined by carefully removing the bottom clamp and opening the drain opening of the pouch to allow the lump of beans paste to fall free of the pouch. Drain time was measured from the moment the lower end of the pouch with its drain opening was allowed to hang free until the lump of beans paste dropped from the pouch.

Thereafter, the drain outlet of each pouch was wiped clean and the pouch was reloaded with an additional mass of beans paste, and the operations described above were repeated.

The results of these tests with time being indicated in (minutes): (seconds): (hundredths of a second) are as follows:

| | 1<br>Dry Pouch | 2<br>Pouch with LD | 3<br>Pouch with LD |
|---|---|---|---|
| Amount of LD added | 0.0 g | 5.102 g | 5.452 g |
| 1$^{st}$ Load Wt Amount of Beans Paste | 21.058 g | 21.192 g | 21.084 g |
| Drop time | 0:59:94 | 0:27:07 | 0:21:50 |
| 2$^{nd}$ Load Wt Amount of Beans Paste | 21.218 g | 21.115 g | 21.113 g |
| Drop time | 0:16:41 | 0:04:32 | 0:01:91 |
| 3$^{rd}$ Load Wt Amount of Beans Paste | 21.040 g | 21.129 g | 21.055 g |
| Drop time | 0:21:40 | 0:04:72 | 0:01:31 |
| Drain time | Did not fall by itself even at 5 min. Had to squeeze out. Messy to clean the pouch outlet. | 0:12:15 | 0:08:75 |
| Amount of LD reloaded | 0.0 g | 5.970 g | 5.388 g |
| 1$^{st}$ Load Wt Amount of Beans Paste | 21.07 g | 21.369 g | 21.184 g |
| Drop time | 01:15:53 | 0:39:78 | 0:00:88 |
| 2$^{nd}$ Load Wt Amount of Beans Paste | 21.416 g | 21.246 g | 21.028 g |
| Drop time | 0:07:44 | 0:04:22 | 0:01:25 |
| 3$^{rd}$ Load Wt Amount of Beans Paste | 21.125 g | 21.165 g | 21.113 g |
| Drop time | 0:47:00 | 0:01:18 | 0:01:56 |
| Drain time | Did not fall by itself at 5 min. Had to squeeze it out. | 0:32:56 | 0:14:00 |

EXAMPLE 5

To test the deodorizing effectiveness of the lubricating deodorants prepared in accordance with Examples 1 and 3, such solutions were compared with results produced by a known copper citrate liquid deodorizer (Hollister M9 prop Deodorizer) capable of complexing with odor-causing molecules and prepared in accordance with Maurer U.S. Pat. No. 6,200,939. The M9 odor neutralizer is known to be effective in reducing or neutralizing malodors produced by a wide variety of materials and is marketed as a liquid that may be added in drop form to ostomy pouches for the purpose of eliminating or reducing fecal odors.

The test was conducted as follows: Weighed 2 g of chopped onions were placed in each of 12 jars, and lids were then attached. (Chopped onions are widely used in test procedures involving fecal odors because sulfur compounds are largely responsible for the odors of both.) The jars were divided into three groups (A, B and C) with each jar being labeled with an alphanumeric code. In each group, one of the jars was kept untreated with a deodorant for purposes of serving as a control. The other three jars in each group were treated with three different deodorant formulations, one being the lubricating deodorant of Example 1 (LD Ex. 1), the second with the lubricating deodorant of Example 3 (LD Ex. 3) and the third with the commercial prop Deodorizer marketed as M9. In the case of M9, nine drops were added to each jar based on the product's label instructions.

Twenty adult human subjects participated in the tests, all of which were carried out under a fume hood. The hood fan was turned on for brief periods between each sample sniffing (prior to opening a jar) to make sure that there would be no residual odor in the atmosphere that might interfere with the test.

The participants were asked to remove the lid of each jar, sniff the contents, and score it for onion odor on a scale of 0 to 4, with score "0" representing No Odor and score "4" representing a Strong Odor. Between each evaluation, the participants sniffed ajar containing fresh ground coffee to clear the nose of any residual onion odor prior to evaluating the next test jar.

The scores of these tests are set forth in the chart below. The chart reveals that jars containing the lubricating deodorant of Example 1 generally produced less detectable odor than those containing the lubricating deodorant of Example 3 or the M9 deodorant. There was no statistical difference in performance between the jars containing the commercial M9 Drop Deodorizer and those containing the lubricating deodorizer using vegetable protein extract as set forth in Example 3.

| LD Ex. 1 | | | | LD Ex. 3 | | | | M9 | | | |
| --- | --- | --- | --- | --- | --- | --- | --- | --- | --- | --- | --- |
| Participant | A | B | C | Participant | A | B | C | Participant | A | B | C |
| 1 | 2 | 1 | 1 | 1 | 1 | 1 | 2 | 1 | 2 | 2 | 2 |
| 2 | 2 | 2 | 2 | 2 | 3 | 2 | 2 | 2 | 3 | 2 | 2 |
| 3 | 3 | 3 | 3 | 3 | 4 | 3 | 2 | 3 | 1 | 2 | 2 |
| 4 | 0 | 0 | 1 | 4 | 1 | 2 | 0 | 4 | 2 | 1 | 2 |
| 5 | 2 | 1 | 1 | 5 | 2 | 4 | 3 | 5 | 2 | 1 | 2 |
| 6 | 2 | 2 | 2 | 6 | 4 | 3 | 3 | 6 | 3 | 3 | 4 |
| 7 | 1 | 1 | 1 | 7 | 3 | 2 | 2 | 7 | 1 | 1 | 2 |
| 8 | 0 | 1 | 0 | 8 | 1 | 2 | 1 | 8 | 2 | 0 | 1 |
| 9 | 1 | 2 | 2 | 9 | 2 | 2 | 2 | 9 | 1 | 3 | 2 |
| 10 | 0.5 | 2 | 1 | 10 | 2 | 3 | 2 | 10 | 1 | 3 | 1 |
| 11 | 1 | 0 | 1 | 11 | 1 | 0 | 0 | 11 | 1 | 1 | 0 |
| 12 | 1 | 1 | 2 | 12 | 2 | 2 | 3 | 12 | 1 | 0 | 1 |
| 13 | 0 | 0 | 0 | 13 | 0 | 3 | 1 | 13 | 2 | 1 | 1.5 |
| 14 | 1 | 1 | 0.5 | 15 | 3 | 3 | 3 | 14 | 2 | 2 | 0.5 |
| 15 | 2 | 1 | 2 | 15 | 3 | 2 | 2 | 15 | 3 | 3 | 3 |
| 16 | 3 | 3 | 3 | 16 | 2 | 2 | 4 | 16 | 3 | 2 | 2 |
| 17 | 3 | 2 | 2 | 17 | 3 | 2 | 1 | 17 | 3 | 3 | 3 |
| 18 | 1 | 0 | 0 | 18 | 2 | 1 | 1 | 18 | 1 | 3 | 2 |
| 19 | 0 | 0 | 0 | 19 | 4 | 2 | 2 | 19 | 2 | 2 | 0 |
| 20 | 1 | 1 | 2 | 20 | 3 | 3 | 3 | 20 | 1 | 2 | 1 |

While in the foregoing we have disclosed embodiments of the invention in considerable detail for purposes of illustration, it will be understood by those skilled in the art that many of these details may be varied without parting from the spirit and scope of the invention.

The invention claimed is:

1. A lubricating deodorant for ostomy pouches consisting of an aqueous solution of
   about 0.1 to about 5.0 percent of total solution weight of a water-soluble cellulosic lubricating agent capable of wetting and clinging to interior wall surfaces of polymeric film materials of an ostomy pouch, said lubricating agent comprising a polymeric water thickener which becomes slippery when hydrated,
   about 0.2 to about 7 percent of total solution weight of a compatible water-soluble complexing agent capable of complexing with and neutralizing the odor-causing molecules of fecal matter, wherein the water-soluble complexing agent is selected from the group consisting of n-ethyl-n-soya-morpholinium ethosulfate, vegetable protein extract and copper citrate,
   up to about 15 percent of total solution weight of one or more surfactants selected from the group consisting of octoxynol-9, poloxamer 188, sorbitan monolaurate, and alkyl dimethylamine oxide,
   about 0.5 to about 20 percent of total solution weight of a humectant-solvent,
   about 0.03 to about 1.0 percent of total solution weight of a preservative,
   about 58 to about 98 percent of total solution weight of water, and
   a pH adjuster or buffer for maintaining said solution at a substantially neutral pH, wherein the lubricating deodorant in aqueous solution is configured to wet, lubricate, and cling to interior wall surfaces of an ostomy pouch and neutralize fecal odor when applied on the interior wall surfaces of the ostomy pouch.

2. The lubricating deodorant of claim 1 in which said complexing agent is also a surfactant that enhances the ability of said lubricating agent to wet the interior surfaces of an ostomy pouch.

3. The lubricating deodorant of claim 1 in which said lubricating agent is selected from the group consisting of hydroxyethylcellulose, hydroxypropylmethylcellulose and hydroxypropylcellulose, and combinations thereof.

* * * * *

UNITED STATES PATENT AND TRADEMARK OFFICE
CERTIFICATE OF CORRECTION

PATENT NO. : 9,259,512 B2
APPLICATION NO. : 12/038623
DATED : February 16, 2016
INVENTOR(S) : Bettakeri Subraya Udayakumar et al.

Page 1 of 1

It is certified that error appears in the above-identified patent and that said Letters Patent is hereby corrected as shown below:

In the Specification

Column 6, line 43, "prop" to read as --Drop--.

Column 6, line 63, "prop" to read as --Drop--.

Signed and Sealed this
Nineteenth Day of July, 2016

Michelle K. Lee
*Director of the United States Patent and Trademark Office*